United States Patent [19]
Szyszkowski

[11] Patent Number: 5,282,841
[45] Date of Patent: Feb. 1, 1994

[54] IMPLANTABLE STIMULATION DEVICE AND METHOD OF MAKING SAME

[75] Inventor: Andrew J. Szyszkowski, Canyon Country, Calif.

[73] Assignee: Siemens Pacesetter, Inc., Sylmar, Calif.

[21] Appl. No.: 961,109

[22] Filed: Oct. 14, 1992

Related U.S. Application Data

[62] Division of Ser. No. 720,078, Jun. 24, 1991, which is a division of Ser. No. 439,070, Nov. 20, 1989, Pat. No. 5,067,903.

[51] Int. Cl.⁵ ............................................. A61N 1/362
[52] U.S. Cl. .................................... 607/36; 607/37
[58] Field of Search .................................... 128/419 P

[56] References Cited

U.S. PATENT DOCUMENTS

| | | | |
|---|---|---|---|
| 3,683,932 | 8/1972 | Cole | 128/419 |
| 3,735,766 | 5/1973 | Bowers et al. | 128/419 |
| 3,757,789 | 9/1973 | Shanker | 128/419 |
| 3,760,332 | 9/1973 | Berkovits et al. | 339/66 |
| 3,866,616 | 2/1975 | Purdy et al. | 128/419 |
| 3,908,668 | 9/1975 | Bolduc | 128/419 |
| 3,951,154 | 4/1976 | Hartlaub | 128/419 |
| 4,010,759 | 3/1977 | Boer | 128/419 |
| 4,027,678 | 6/1977 | von Oostyeen et al. | 129/419 |
| 4,072,154 | 2/1978 | Anderson et al. | 128/419 |
| 4,105,037 | 8/1978 | Richter et al. | 128/419 |
| 4,142,532 | 3/1979 | Ware | 128/419 |
| 4,152,540 | 5/1979 | Duncan et al. | 128/419 |
| 4,182,345 | 1/1980 | Grose | 128/419 |
| 4,202,592 | 5/1980 | Rullier et al. | 128/419 |
| 4,226,244 | 10/1980 | Coury et al. | 128/419 |
| 4,278,093 | 7/1981 | Lafortune et al. | 128/419 |
| 4,310,001 | 1/1982 | Comben | 128/419 |
| 4,445,511 | 5/1984 | Cowoery et al. | 128/419 |
| 4,456,786 | 6/1984 | Kyle | 128/419 |
| 4,603,696 | 8/1986 | Cross, Jr. et al. | 128/419 |
| 4,712,557 | 12/1987 | Harris | 128/419 |
| 5,103,818 | 4/1992 | Maston et al. | 128/419 P |

*Primary Examiner*—William E. Kamm
*Assistant Examiner*—Scott M. Getzow
*Attorney, Agent, or Firm*—Lisa P. Weinberg

[57] ABSTRACT

A ribbon conductor set and related method of production and installation are provided for electrically interconnecting components in an implantable medical device, such as a heart pacemaker unit or the like. The ribbon conductor set is formed by die cutting and/or stamping a thin plate of conductive material to define a plurality of conductor ribbons supported from a frame. The ribbon set and supporting frame are shaped for seated placement into a fixture to orient the conductor ribbons in predetermined array to extend between electrical components on the fixture, such as between connector blocks and feedthrough terminals of a heart pacemaker unit. The fixture thus supports the conductor ribbons for facilitated connection to the electrical components, such as by welding, after which the resultant subassembly may be further processed as by encapsulation within a cast epoxy head or the like.

10 Claims, 3 Drawing Sheets

IMPLANTABLE STIMULATION DEVICE AND METHOD OF MAKING SAME

CROSS-REFERENCE TO RELATED PATENT APPLICATIONS

This application is a division of copending application entitled "Implantable Stimulation Device and Method of Making Same," Ser. No. 07/720,078, filed Jun. 24, 1991, which is a division of a prior copending application Ser. No.07/439,070, filed Nov. 20, 1989, which issued as U.S. Pat. No. 5,067,903, and from which benefit of earlier filing date is claimed under 35 USC 120.

BACKGROUND OF THE INVENTION

This invention relates generally to improvements in devices and methods for conductively interconnecting electrical components in an implantable medical device or the like. More particularly, this invention relates to a conductor set and related production and installation method for quickly and easily interconnecting multiple electrical components. The invention is particularly designed to facilitate electrical interconnection of pacemaker lead connector blocks with feedthrough terminals of an implantable heart pacemaker unit or similar device.

Implantable medical devices of the type having electrical circuit components are well known in the medical arts. In one particularly common form, the implantable device comprises a pacemaker unit having an appropriate electrical power supply and related control circuitry for use in electrically stimulating a patient muscle, such as the heart. Such pacemaker unit commonly includes an hermetically sealed case or housing within which the power supply and control circuitry are protectively encased, in combination with one or more conductive pacemaker leads extending from the housing to the selected muscle structure within the patient. Feedthrough terminals on the pacemaker housing accommodate hermetically sealed passage of electrical conductors to the housing exterior for appropriate connection to the pacemaker lead or leads, typically through the use of so-called connector blocks having set screws or the like for secure lead attachment. The connector blocks and associated feedthrough conductors disposed externally of the pacemaker housing are commonly encased within an hermetically sealed head structure, such as an insulative head of cast epoxy or the like.

In the past, considerable research and development activity has focused upon the design of feedthrough terminals for permitting pacing signals to be transmitted from the hermetically sealed unit housing. Similarly, significant efforts have been directed toward the design of pacemaker lead connector blocks for obtaining a secure yet hermetically sealed electromechanical connection to pacemaker leads. However, comparatively little attention has been directed to the design of conductors and related installation methods for electromechanically interconnecting the feedthrough terminals with the associated lead connector blocks. To the contrary, available pacemaker units have predominantly utilized elongated wires extending from the feedthrough terminals and individually shaped by bending for appropriate connection by welding or the like to the associated connector blocks. Unfortunately, the close working space provided in a desirably compact implantable device makes this wire bending and shaping procedure both tedious and time consuming. Moreover, in pacemaker units having multiple feedthrough terminal conductors, significant attention and skill are required to maintain the conductor wires in sufficiently spaced array to avoid short circuit failures during pacemaker unit operation.

There exists, therefore, a significant need for improvements in devices and methods for electrically interconnecting feedthrough terminals with lead connector blocks in a heart pacemaker unit or other implantable medical device, particularly with respect to permitting the desired electrical interconnections to be made quickly and easily with multiple conductors arranged and maintained in spaced relation to prevent short circuit failures. The present invention fulfills these needs and provides further related advantages.

SUMMARY OF THE INVENTION

In accordance with the invention, a ribbon conductor set is provided for facilitated electrical connection of feedthrough terminals and lead connector blocks in an implantable medical device, such as a heart pacemaker unit or the like. The ribbon conductor set comprises a plurality of conductor ribbons formed as a set in predetermined number, spacing, and geometry to extend between multiple conductors at one or more feedthrough terminals and a plurality of lead connector blocks individually associated with the feedthrough conductors. The conductor ribbons are adapted for installation as a group into a pacemaker unit, and in an orientation which accommodates relatively simple connection to the feedthrough terminals and connector blocks by spot welding or the like.

In accordance with the preferred apparatus and method corresponding with the invention, the ribbon conductor set comprises the plurality of conductor ribbons formed from conductive sheet stock by etching and/or appropriate die cutting. The conductor ribbons are arranged in spatial array to avoid short circuit contact therebetween and further to have individualized shapes each adapted for connection between a designated feedthrough terminal conductor and associated lead connector block of the pacemaker unit. The conductor ribbons are initially supported by narrow frets from a support frame which is also formed from the conductive sheet stock. A stamping step is typically included to provide the conductor ribbons with a three-dimensional shape as may be required for connection in mutually spaced array to the feedthrough terminal conductors and lead connector blocks. Additional spacer means such as a bead of an insulative epoxy and/or a strip of insulative tape may be applied to the conductor ribbons to maintain the ribbons in spaced relation during handling and installation.

A fixture is provided for supporting a pacemaker unit housing having feedthrough terminals thereon in predetermined positional relation to pacemaker lead connector blocks. In this regard, the fixture includes locator means for receiving and supporting the housing and the connector blocks at the predetermined relative positions. The ribbon conductor set is then placed over the pacemaker housing and the lead connector blocks, with the support frame and fixture including registration means such as a locator pin received into a frame aperture for accurately positioning the ribbon set. The individual conductor ribbons are each exposed in this manner for easy access and fixation to the feedthrough terminals and connector blocks by spot welding or the like. The support frame is then easily removed from the conductor ribbons by trimming at the frets, whereupon the entire subassembly including the conductor ribbons, connector blocks and feedthrough terminals may be encapsulated within an insulating head of cast epoxy or the like.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 4 is a perspective view of a fixture for use in mounting the ribbon conductor set into a pacemaker unit or the like;

DETAILED DESCRIPTION OF THE PREFERRED EMBODIMENT

Figure 1:
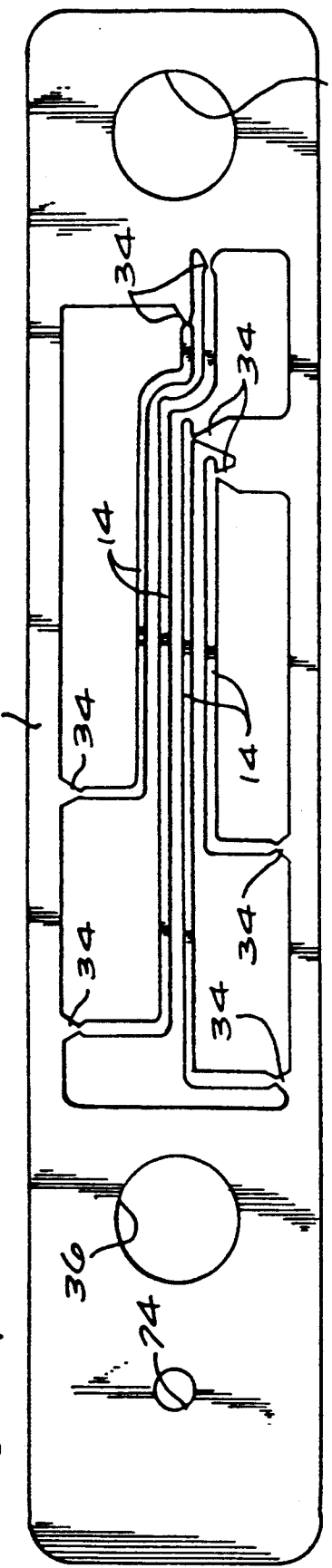
FIG. 1 is a plan view of a ribbon conductor set embodying the novel features of the invention, and illustrating the ribbon conductor set supported within an integrally formed frame.
Figure 8:
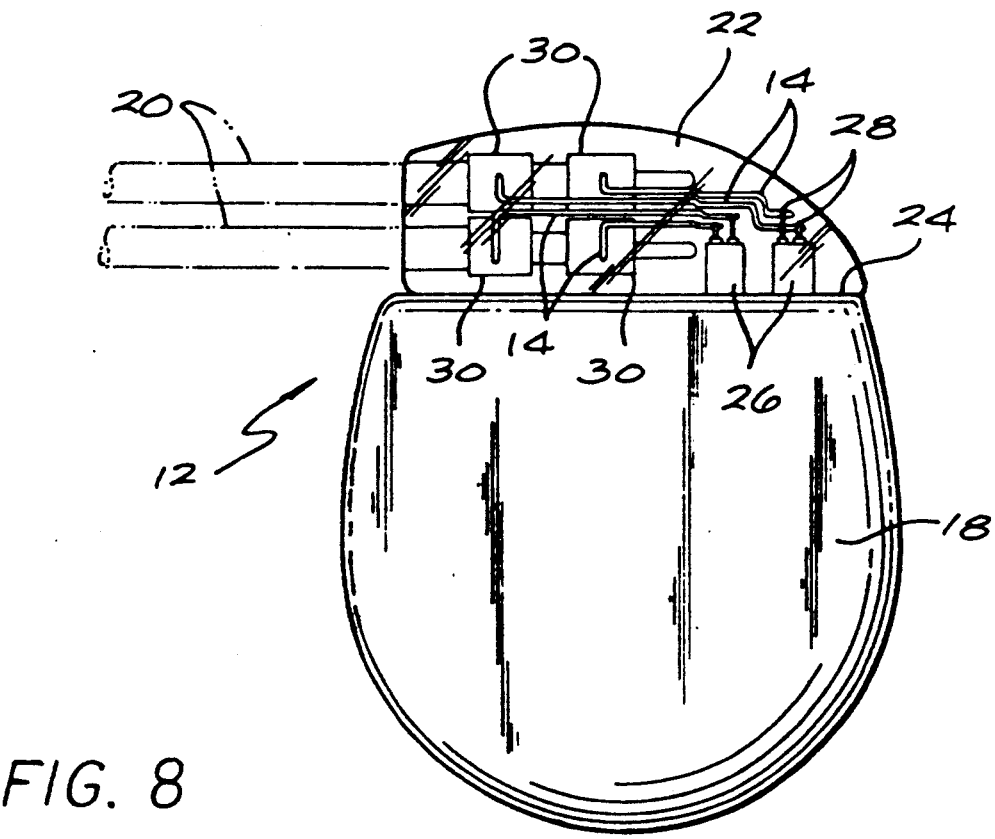
FIG. 8 is a front elevational view of a resultant finished pacemaker unit having the feedthrough terminals, the ribbon conductor set, and the connector blocks encapsulated within a cast head of a suitable insulative epoxy.

As shown in the exemplary drawings, a ribbon conductor set referred to generally in FIG. 1 by the reference numeral 10 is provided for quickly and easily interconnecting electrical components in an implantable medical device, such as a heart pacemaker unit 12 or the like as viewed in FIG. 8. The ribbon conductor set 10 provides a plurality of conductor ribbons 14 in a predetermined shape and spatial array in accordance with the geometry of the electrical components to be interconnected. This shaped array of conductor ribbons 14 is supported as a unit or group by an integral support frame 16 for facilitated handling and placement in the course of connection to the associated electrical components.

The ribbon conductor set 10 of the present invention is designed particularly for use in an implantable medical device such as a heart pacemaker unit 12 (FIG. 8) In this regard, heart pacemaker units are generally known in the art for use in electrical stimulation of the heart muscle to regulate patient heartbeat in a controlled manner. The pacemaker unit 12 normally includes an appropriate power source and related electronic circuitry encased within a compact, hermetically sealed housing or case 18 adapted for implantation directly into the body of a patient at a selected convenient location. The unit produces a timed sequence of pacing pulses which are coupled to one or more conductive pacemaker leads 20, with the illustrative drawings depicting the pacemaker unit 12 to include a pair of pacemaker leads 20 for so-called duplex mode operation. The pacemaker leads 20 extend from the unit housing 18 for implantation of their distal ends (not shown) into target muscle tissue to be stimulated.

As shown best in FIG. 8, the pacemaker unit 12 includes a head 22 on the unit housing 18, wherein the head 22 includes means for electromechanically anchoring the pacemaker leads 20 in conductive relation with the pacing signals generated by the circuitry components within the housing 18. More specifically, the pacemaker housing 18 defines a relatively flat mounting platform 24 at one edge thereof. One or more so-called feedthrough terminals 26 project upwardly from this platform and provide hermetically sealed structures of a type known in the art for passing electrical conductors from the interior of the housing 18. The illustrative drawings show a pair of feedthrough terminals 26 each including a pair of short upstanding conductors 28, thereby providing a total of four conductors 28 for use in duplex mode pacemaker unit operation. These feedthrough terminal conductors 28 are respectively connected by means of the ribbon conductor set 10 of the present invention to a corresponding set of four connector blocks 30 adapted for electromechanical connection to the pacemaker leads 20. Subsequent to electrical interconnection of the feedthrough terminal conductors 28 with the connector blocks 30, as will be described in more detail, these components are encapsulated within a block of insulative epoxy material or the like which is cast in place to define the head 22 maintaining the various components in the desired hermetically sealed and predetermined interspatial relation.

The apparatus and method of the present invention is designed to facilitate the process of interconnecting the feedthrough terminal conductors 28 with the connector blocks 30. More particularly, the ribbon conductor set 10 provides a preshaped and prespaced array of conductive elements which can be handled as a unitary set or group for rapid yet accurate placement and appropriate connection by resistance spot welding or the like. The ribbon set 10 is adapted for cost-efficient manufacture by die cutting and/or stamping processes to yield detailed yet reproducible ribbon shapes in conformance with the geometry of the feedthrough terminals and connector blocks to be interconnected. Importantly, when the ribbon set is mounted in place, the individual conductor ribbons 14 are maintained in sufficient spacing to substantially eliminate risk of short circuit failures.

With reference to FIG. 1, the ribbon conductor set 10 is formed from sheet stock of a suitable conductive material to include the set of conductor ribbons 14 carried within the surrounding support frame 16. As shown in the initial stages of formation, the support frame 16 is generally coplanar with the conductor ribbons 14, with each ribbon 14 having an individualized elongated shape supported at its opposite ends by a pair of narrow frets 34 on the support frame 16. In a preferred method of formation, this frame and ribbon set combination is formed by etching thin sheet stock of stainless steel or platinum alloy or the like to produce the desired ribbon pattern, wherein this etched sheet stock may have a thickness on the order of a few thousandths of an inch. Alternately, cutting and/or stamping processes may be used. Desirably, the support frame 16 includes one or more large ports 36 formed therein to permit accurate placement into process tools and fixtures.

Figure 2:
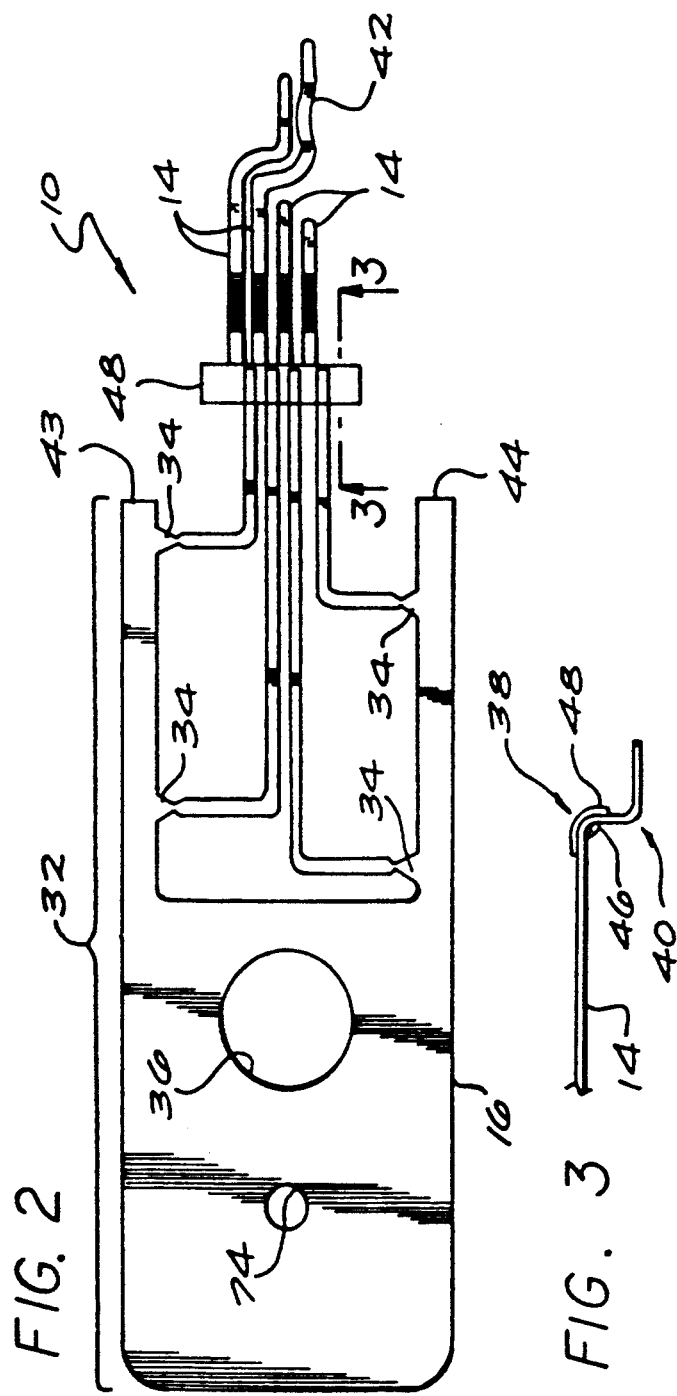
FIG. 2 is a plan view of the ribbon conductor set similar to FIG. 1, but illustrating the ribbon conductor set subsequent to die cutting and shaping; and removal of a portion of the support frame.
Figure 3:
FIG. 3 is a fragmented elevational view taken generally on the line 3—3 of FIG. 2.
Figure 4:
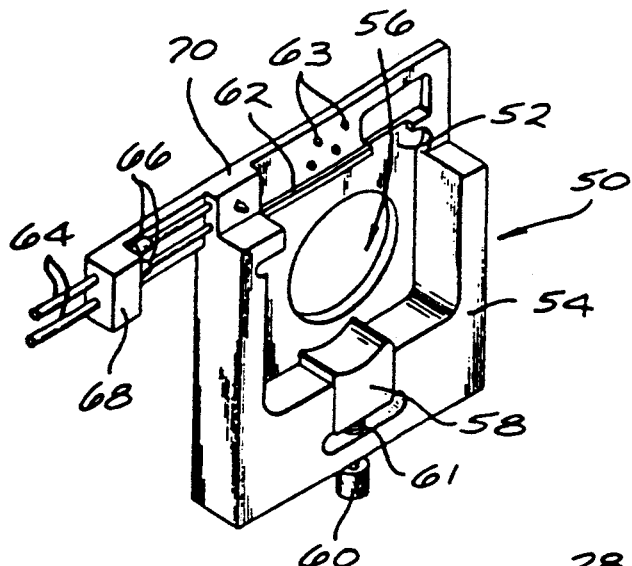

FIGS. 2 and 3 illustrate the ribbon conductor set 10 subsequent to a stamping and cutting process step for shaping the individual conductor ribbons 14 to an appropriate three-dimensional geometry. More specifically, the ribbon set can be seated into an appropriate die tool for shaping each ribbon 14 to include one or more bends deviating from the plane of the support frame 16. FIG. 3 illustrates all four ribbons 14 to include a common rearward bend 38 in close association with a return bend 40. In addition, FIG. 2 shows one of the ribbons 14 to include a generally semicircular bend 42 for clearance with a feedthrough terminal 26, as will become more apparent. During this die stamping step, a portion of the support frame 16 is desirably removed by trimming the frame at points 43 and 44, and by severing the frets 34 at one common end of the conductor ribbons 14. As a result, the conductor ribbons 14 project generally in somewhat cantilevered relation from the remaining portion of the support frame 32 which remains connected to the ribbons by means of the remaining frets 34.

The conductor ribbons 14 are desirably provided with additional support means to maintain the inter-ribbon spacing and to minimize risk of ribbon damage during subsequent handling. For example, as shown in FIG. 3, an elongated bead 46 of epoxy or the like may be placed and cured along the conductor ribbons 14 such as at the inboard side of the bend 38 to support the ribbons with respect to each other. Alternatively, or in addition, a strip of tape 48 such as insulating tape of Kapton film or the like may be used as a temporary support for the fragile ribbons 14.

Figure 5:
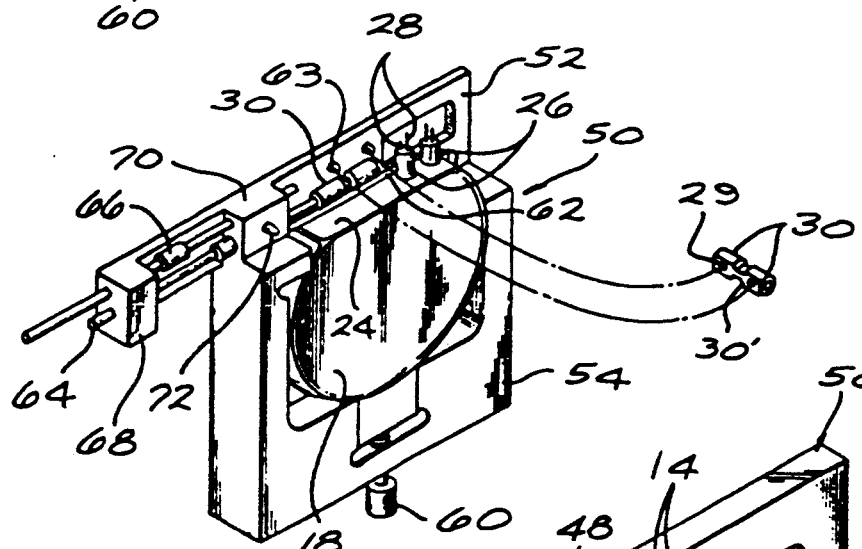
FIG. 5 is a perspective view of the fixture similar to FIG. 4, but showing a pacemaker unit housing and pacemaker lead connector blocks mounted within the fixture in predetermined relative positions.

A fixture 50 is depicted in FIGS. 4–7 for use in supporting the various components in a convenient arrangement during placement and mounting of the ribbon conductor set 10. More particularly, the illustrative fixture 50 includes a base plate 52 which cooperates with a short upstanding and generally U-shaped base wall 54 to define an open-sided cavity 56 (FIG. 4) for receiving the housing 18 of the pacemaker unit 12. A spring-loaded foot 58 is centrally located along the base wall 54 at a position opposite the open side thereof, and can be suitably manipulated by a knob 60 or the like and related spring 61 to press against the unit housing 18. This pressing action of the foot 58 advances one side edge of the housing platform 24 into seated relation with a short upstanding rib 62 on the base plate 52, thereby positively and firmly locking the unit housing 18 in a predetermined orientation within the fixture 50 (FIG. 5). Such placement of the unit housing 18 additionally positions the feedthrough terminals 26 and their respective short protruding conductors 28 at predetermined locations within the fixture.

The connector blocks 30 are also mounted into the fixture 50 at predetermined positions. In this regard, as shown in FIG. 5, the connector blocks 30 are traditionally provided in interconnected pairs with each connector block having a flat rear face 30' with a shallow threaded bore 29 formed therein. These threaded bores 29 are intended for subsequent reception of set screws (not shown) for use in locking connection to the pacemaker leads 20. At this stage, however, the threaded bores 29 in the connector blocks 30 are open and provide convenient receptacles for short positioning pins 63 on the fixture base plate 52, such that the connector blocks 30 are predeterminably positioned relative to the feedthrough terminals 26. Additional anchoring of the pairs of connector blocks 30 may be provided by temporary insertion of lead pins 64 into the connector blocks, wherein these lead pins 64 are conveniently mounted on the fixture for retractable movement limited by enlarged pin spools 66 adapted to abut a pair of raised stops 68 and 70.

Figure 6:
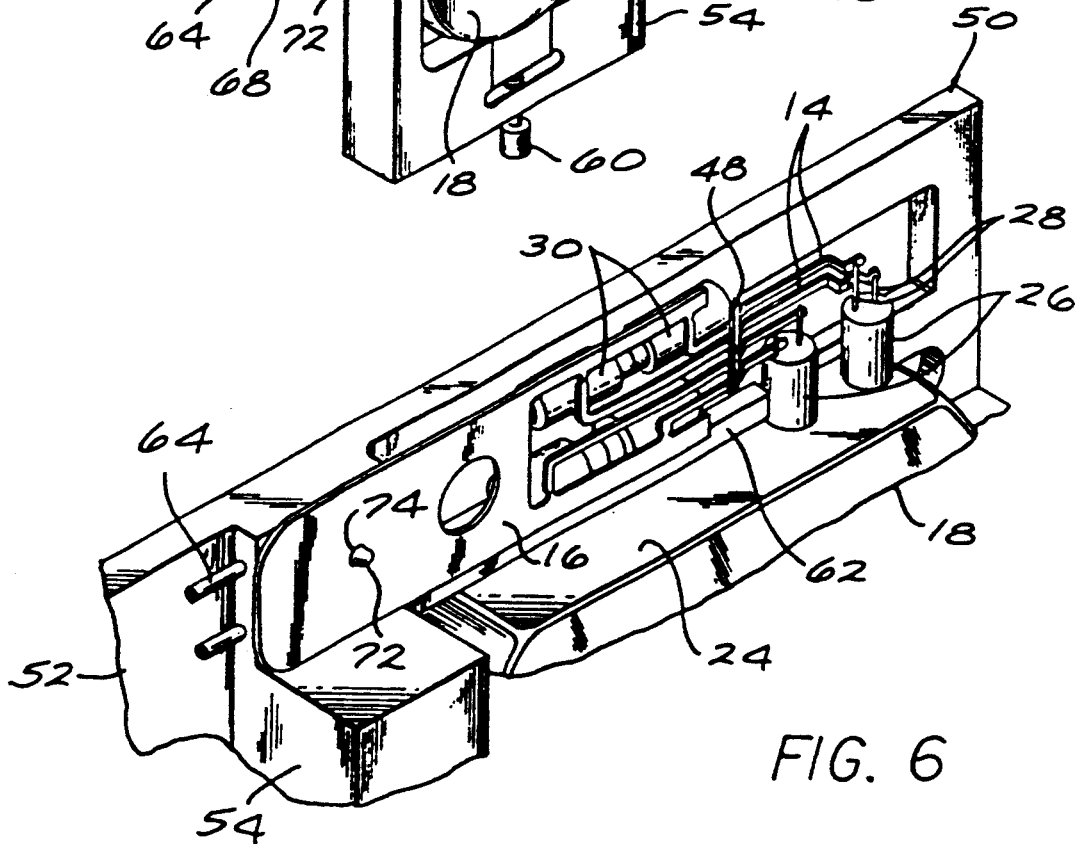
FIG. 6 is an enlarged fragmented perspective view corresponding with an upper region of the fixture as depicted in FIG. 5, but showing the ribbon conductor set placed onto the fixture in a position overlying the pacemaker housing and the lead connector blocks.
Figure 7:
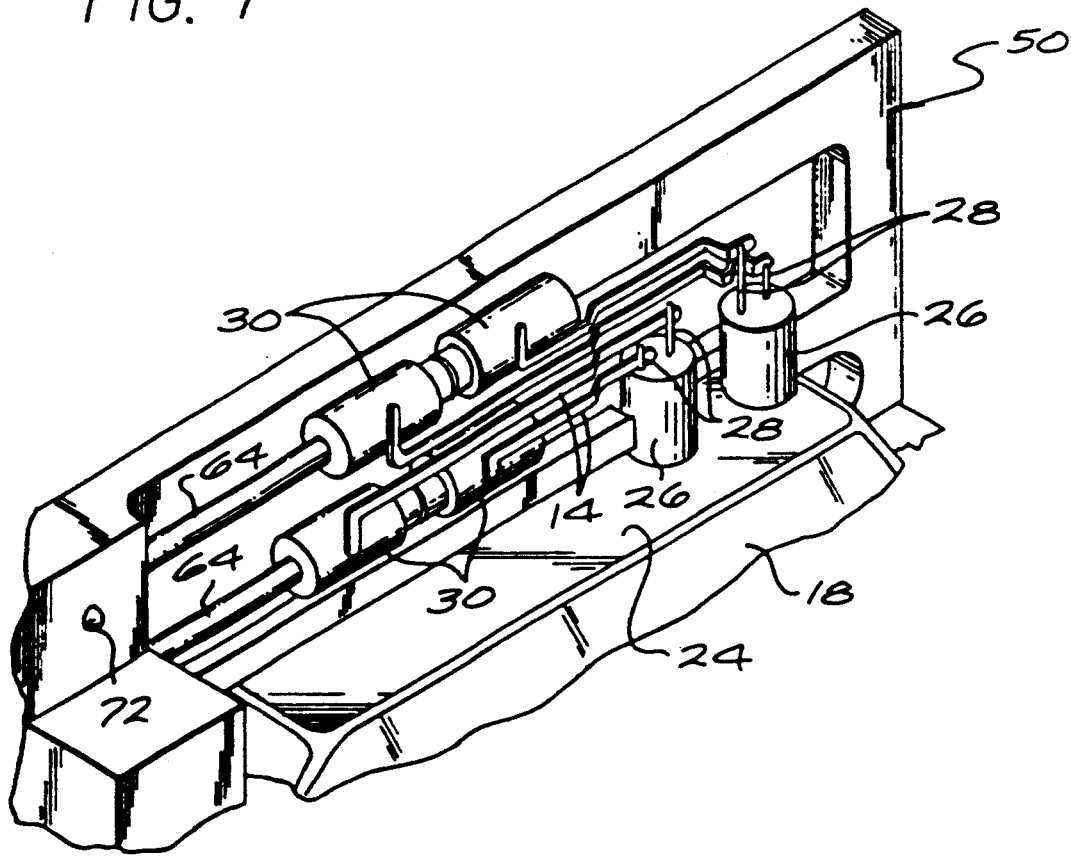
FIG. 7 is an enlarged fragmented perspective view similar to FIG. 6, and showing the ribbon conductor set electrically interconnecting the lead connector blocks with feedthrough terminal conductors, and with the support frame for the ribbon set being removed.

With the pacemaker unit housing 18 and the connector blocks 30 in place, the ribbon conductor set 10 is easily placed in overlying relation over the pacemaker components. A short locator pin 72 on the fixture 50 is adapted for reception into a mating aperture 74 in the support frame 16 to predetermine the position of the ribbon set (FIG. 6). In this position, the free ends of the individual conductor ribbons 14 align easily and accurately with the respective feedthrough terminal conductors 28, and the opposite fret-supported ends of the ribbons 14 align with the respective connector blocks 30. In this orientation, both ends of each ribbon 14 can be attached quickly and easily to the associated components by resistance spot welding or the like, and the remainder portion of the support frame 16 can be removed quickly and easily by severing at the frets 34. The strip of support tape 48, if used, may be removed at a convenient time typically subsequent to ribbon attachment to the underlying components.

The resultant head subassembly, including the connector blocks 30 interconnected via the conductor ribbons 14 with the feedthrough conductors 28, provides an accurate and highly attractive electrical interconnection. The pacemaker unit 12 including this head subassembly is removed from the fixture 50 and appropriately processed to cast the epoxy head 22. This head 22, as viewed in FIG. 8, encapsulates the electrical components with an insulative and hermetic seal material. This epoxy head further supports the components in the desired predetermined spatial relation, and in a manner which is fully compatible with the epoxy bead 46 (FIG. 3) used to support the ribbons 14 during processing.

The ribbon conductor set 10 thus provides a simple apparatus and method for facilitated and accurate electrical interconnection of feedthrough terminals and lead connector blocks in a heart pacemaker or the like. The conductor ribbons 14 are preformed in a manner consistent with economical production processes, and in a manner permitting handling as a unitary group during installation procedures.

A variety of modifications and improvements to the ribbon conductor set 10 and related installation method will be apparent to those persons skilled in the art. Accordingly, no limitation on the invention is intended by way of the foregoing description and the accompanying drawings, except as set forth in the appended claims.

What is claimed is:

1. An implantable stimulating device for stimulating a patient's heart, comprising:
   a battery;
   a pulse generator, coupled to the battery, for generating stimulating pulses to the patient's heart;

a hermetically sealed housing for housing the battery and the pulse generator, the housing including a plurality of feedthrough terminal pins for connecting the pulse generator to the exterior of the housing;

a plurality of connector blocks disposed external to the housing for securing at least one stimulation lead thereto;

a plurality of conductor ribbons formed as a set in a predetermined number, shape and spacing, the conductor ribbons extending between respective ones of the connector blocks and the feedthrough terminal pins; and encapsulation means attached to the housing, the encapsulation means having the plurality of connector blocks and the plurality of conductor ribbons encapsulated therein, the encapsulation means further having at least one channel for receiving at least one stimulating lead therein.

2. The implantable stimulation device of claim 1, wherein the encapsulation means comprises epoxy.

3. The implantable stimulation device of claim 1, wherein the conductor ribbons are generally elongated in shape.

4. The implantable stimulation device of claim 1, wherein the conductor ribbons comprise a selected conductive material.

5. The implantable stimulation device of claim 4, wherein the selected conductive material is stainless steel.

6. The implantable stimulation device of claim 4, wherein the selected conductive material is platinum alloy.

7. The implantable stimulation device of claim 4, wherein the conductor ribbons have a three-dimensional geometry.

8. The implantable stimulation device of claim 7, wherein the conductor ribbons have at least one bend point.

9. The implantable stimulation device of claim 8, wherein the bend point defined by the conductor ribbons is a semicircular bend for clearance with a feedthrough terminal.

10. The implantable stimulation device of claim 8, further comprising an epoxy bead spacer mounted onto the conductor ribbons generally on one side of the bend point defined by the conductor ribbons.

* * * * *